(12) United States Patent
Fino et al.

(10) Patent No.: US 6,828,448 B2
(45) Date of Patent: Dec. 7, 2004

(54) METHANESULPHONAMIDO-BENZOFURAN, PREPARATION METHOD AND USE THEREOF AS SYNTHESIS INTERMEDIATE

(75) Inventors: Noël Fino, Château-Arnoux (FR); Corinne Leroy, Orpierre (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/450,312

(22) PCT Filed: Dec. 10, 2001

(86) PCT No.: PCT/FR01/03899
§ 371 (c)(1),
(2), (4) Date: Jun. 10, 2003

(87) PCT Pub. No.: WO02/48132
PCT Pub. Date: Jun. 20, 2002

(65) Prior Publication Data
US 2004/0048921 A1 Mar. 11, 2004

(30) Foreign Application Priority Data
Dec. 11, 2000 (FR) .......................................... 00 16070

(51) Int. Cl.$^7$ .................... C07D 307/79; C07D 307/80; C07D 307/81; C07D 333/58
(52) U.S. Cl. ........................ 549/471; 549/462; 549/467; 549/469
(58) Field of Search .................. 549/471, 462, 549/467, 469

(56) References Cited

U.S. PATENT DOCUMENTS 5,223,510 A    6/1993   Gubin et al. ................ 514/299

FOREIGN PATENT DOCUMENTS

EP   0 471 609 A    2/1992
WO   WO 96 05190 A  2/1996

*Primary Examiner*—Ba K. Trinh
(74) *Attorney, Agent, or Firm*—Paul E. Dupont; Michael D. Alexander

(57) ABSTRACT

The invention relates to 2-butyl-5-(methanesulfonamido) benzofuran, its preparation and its use.

This compound is a synthesis intermediate, in particular for the preparation of dronedarone.

50 Claims, No Drawings

METHANESULPHONAMIDO-BENZOFURAN, PREPARATION METHOD AND USE THEREOF AS SYNTHESIS INTERMEDIATE

The present invention relates, in a general way, to a (methanesulfonamido)benzofuran derivative, to its method of preparation and to its use as a synthesis intermediate.

More precisely, the subject of the invention is 2-butyl-5-(methanesulfonamido)benzofuran of formula:

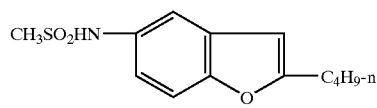

(1)

This compound has proved particularly useful as an intermediate product for the final preparation of (aminoalkoxybenzoyl)benzofuran derivatives, in particular of 2-butyl-3-(4-[3-(dibutylamino)propoxy]-benzoyl)-5-(methanesulfonamido)benzofuran commonly called dronedarone and its pharmaceutically acceptable salts.

This (methanesulfonamido)benzofuran derivative and its pharmaceutically acceptable salts have been described in patent EP0471609 as well as its therapeutic applications. In the cardiovascular field, this compound has proved particularly useful especially as an antiarrhythmic agent.

There has been reported in patent EP0471609, mentioned above, a method for preparing 3-[4-(aminoalkoxy)benzoyl]benzofuran or benzo[b]thiophene derivatives by attaching an aminoalkoxybenzoyl chain to a benzofuran or benzo[b]thiophene derivative, according to which method there is first added to the benzofuran or benzo[b]thiophene derivative in question a benzoyl group containing in the para position an oxygen protected with a methyl group, deprotection is carried out in order to regenerate the hydroxyl functional group and finally the desired aminoalkyl chain is introduced.

More specifically, this method when applied to the preparation of dronedarone comprises the sequence of steps below:

a) reaction of 2-butyl-5-nitrobenzofuran with anisoyl chloride in the presence of tin tetrachloride based on the Friedel-Crafts reaction conditions and hydrolysis to form 2-butyl-3-(4-methoxybenzoyl)-5-nitrobenzofuran, b) demethylation of the compound thus obtained in the presence of 2.25 molar equivalents of aluminum chloride and hydrolysis so as to form 2-butyl-3-(4-hydroxybenzoyl)-5-nitrobenzofuran, c) condensation of the compound obtained with 1-chloro-3-(dibutylamino)propane in the presence of potassium carbonate, to give 2-butyl-3-(4-[3-(dibutylamino]propoxylbenzoyl)-5-nitrobenzofuran, d) hydrogenation of the compound thus formed, in the presence of platinum oxide, which gives 5-amino-2-butyl-3-(4-[3-dibutylamino)propoxy]benzoylbenzofuran, e) reaction of the 5-aminobenzofuran derivative thus obtained with methanesulfonyl chloride in the presence of triethylamine, which gives dronedarone.

However, this method is not without some disadvantages because, in particular, of the use of aluminum chloride. Indeed, the use of this method on an industrial scale causes high discharges of aluminum hydroxide whose treatment, in order to avoid problems of pollution, is found to be expensive. In addition, the use of 2-butyl-3-(4-methoxybenzoyl)-5-nitrobenzofuran should be avoided as far as possible because of its mutagenic properties.

However, the desired compound is produced with a maximum yield of 60% from 2-butyl-5-nitrobenzofuran according to this method comprising a relatively large number of steps since at least five steps are necessary for the final formation of dronedarone.

The search for an industrial method for the preparation of dronedarone or its pharmaceutically acceptable salts using easily accessible and inexpensive synthesis intermediates based on a more direct method than the earlier method and not using aluminum chloride therefore remains of unquestionable interest.

There has been reported in J. Med. Chem. 1984, 27, 1057–1066 a more convergent method for attaching an aminoalkoxybenzoyl chain to a benzo[b]thiophene derivative without an intermediate step of protecting/deprotecting the hydroxyl functional group. However, this method still proposes on page 1064 the use of aluminum chloride in particularly large quantities since it is of the order of 9 molar equivalents.

According to this method, the benzo[b]thiophene derivative in question is condensed, in an organic phase consisting of dichloroethane, with the hydrochloride of the chloride of the aminoalkoxybenzoyl derivative, this being in the presence of aluminum chloride.

After hydrolysis, the hydrochloride of the desired 3-[4-(aminoalkoxy)benzoyl]benzo[b]thiophene is recovered partly from the organic phase and partly from the aqueous phase by three extractions with chloroform and then treated with sodium hydroxide.

In the context of the preparation of the present invention, this method is applied starting with 2-butyl-5-nitrobenzofuran in order to directly prepare 2-butyl-3-(4-[3-(dibutylamino)propoxyl]benzoyl)-5-nitrobenzofuran, this being using the following steps:

treatment of 2-butyl-5-nitrobenzofuran by means of 4-[3-(dibutylamino)propoxy]benzoyl chloride hydrochloride in the presence of 9 molar equivalents of aluminum chloride, this being in an organic phase, hydrolysis, recovery of 2-butyl-3-(4-[3-(dibutylamino)propoxy]benzoyl)-5-nitrobenzofuran hydrochloride and treatment with sodium hydroxide so as to form the desired 2-butyl-3-(4-[3-(dibutylamino)propoxy]benzoyl)-5-nitrobenzofuran.

However, this method has proved unsuitable at the industrial level because, on the one hand, of the enormous quantity of aluminum hydroxide thus produced and, on the other hand, of the large amount of impurities recovered and, consequently, of the low yield of 2-butyl-3-(4-[3-(dibutylamino)propoxy]-5-nitrobenzofuran (20 to 30%).

However, it has been found, surprisingly, that it is possible, starting with 2-butyl-5-(methanesulfonamido) benzofuran and using appropriate quantities of a Lewis acid in a Friedel-Crafts reaction, to directly obtain dronedarone hydrochloride with excellent yields since they are at least 85%, it being possible for this hydrochloride to be recovered in a remarkably advantageous manner since it is practically entirely found not in the aqueous phase as might have been predicted but in the organic phase used, which avoids the need to carry out several extractions of this same aqueous phase as in the earlier method.

In addition, the 2-butyl-5-(methanesulfonamido) benzofuran may itself be obtained with great ease and high yields, since they are above 75%, from 5-amino-2-butylbenzofuran and even from the precursor of the latter, namely 2-butyl-5-nitrobenzofuran.

2-Butyl-5-(methanesulfonamido)benzofuran is a novel product which can be easily obtained in crystalline form, unlike 2-butyl-5-nitrobenzofuran whose crystalline state may be difficult to obtain. This methanesulfonamido derivative therefore has an undeniable advantage over the nitro derivative in question.

Consequently, the invention relates to 2-butyl-5-(methanesulfonamido)benzofuran as a novel industrial product useful in particular as synthesis intermediate, for example for the preparation of dronedarone or its pharmaceutically acceptable salts.

Thus, according to the invention, 2-butyl-5-(methanesulfonamido)benzofuran is prepared by reacting 5-amino-2-butylbenzofuran with methanesulfonyl chloride or methanesulfonic anhydride, the reaction taking place in the presence of an acid acceptor such as triethylamine or ammonia, giving the desired compound. Generally, the reaction takes place at room temperature and in one or more apolar solvents preferably chosen from halogenated hydrocarbons and ethers such as, for example, methyl tert-butyl ether, tetrahydrofuran, dichloromethane or dichloroethane.

5-Amino-2-butylbenzofuran, for its part, may be prepared by hydrogenating 2-butyl-5-nitrobenzofuran in the presence of an appropriate catalyst, giving the desired compound.

As catalyst, a platinum derivative such as platinum oxide or an ammonium formate/palladized charcoal system is normally used, the hydrogenation taking place at room temperature and optionally under pressure, for example at a pressure of the order of 20 to 30 bar.

This hydrogenation; which is carried out with excellent yields of up 100%, has unquestionable advantages compared with the hydrogenation of 2-butyl-3-(4-[3-(dibutylamino)propoxy]benzoyl)-5-nitrobenzofuran of the earlier method. Indeed, 2-butyl-5-nitrobenzofuran, apart from the nitro group, contains no other functional group which can be modified by this reaction, unlike the 2-butyl-3-(4-[3-(dibutylamino)propoxy]benzoyl)-5-nitrobenzofuran derivative whose hydrogenation can prove difficult because of the by-products formed.

As indicated above, 2-butyl-5-(methanesulfonamido)benzofuran can be used for the preparation of dronedarone.

Thus, according to the invention, dronedarone is prepared by first forming its hydrochloride, that is to say by reacting, in an organic phase, 2-butyl-5-(methanesulfonamido)benzofuran with 4-[3-(dibutylamino)propoxy]benzoyl chloride hydrochloride, this being in the presence of a Lewis acid as catalyst and by hydrolyzing in order to form dronedarone hydrochloride which is recovered from the organic phase.

The reaction, which is performed under Friedel-Crafts reaction conditions, is normally carried out at room temperature and in an organic phase consisting of one or more solvents chosen from halogenated or nonhalogenated hydrocarbons, preferably of the aliphatic, alicyclic or aromatic type. Generally, halogenated, preferably chlorinated, hydrocarbons of the aliphatic, alicyclic or aromatic type, such as for example dichloromethane, dichloroethane or chlorobenzene, are used.

In addition, the Lewis acid may be aluminum chloride, zinc chloride, boron trifluoride, stannic chloride, titanium tetrachloride or preferably ferric chloride. It is also possible to use a mixture of these Lewis acids. This Lewis acid is used at concentrations which do not exceed 5 molar equivalents, in particular in an amount of 2 to 5 molar equivalents. More particularly, this Lewis acid is used at concentrations which do not exceed 4 molar equivalents. Still more particularly, this Lewis acid is used at concentrations which do not exceed 3 molar equivalents, in particular in an amount of 2 to 3 molar equivalents, preferably 2.5 molar equivalents.

Finally, 4-[3-(dibutylamino)propoxy]benzoyl chloride hydrochloride is used at concentrations of the order of 1 to 1.3 molar equivalents.

The dronedarone hydrochloride thus obtained is then converted, after isolation, to dronedarone by treating with a basic agent such as an alkali metal hydroxide, for example sodium hydroxide, an alkali metal carbonate or an alkali metal hydrogen carbonate such as sodium hydrogen carbonate, which gives the desired compound.

According to a preferred embodiment of the invention, dronedarone is prepared without isolating its hydrochloride which is transiently formed, that is to say in the actual medium where this hydrochloride is prepared.

Consequently, according to one variant of the invention, dronedarone is prepared by means of a method according to which, in an organic phase consisting of one or more solvents chosen from halogenated or nonhalogenated hydrocarbons, 2-butyl-5-(methanesulfonamido)benzofuran is reacted with 4-[3-(dibutylamino)propoxy]benzoyl chloride hydrochloride, this being in the presence of a maximum of 5 molar equivalents, in particular of a maximum of 4 molar equivalents, and preferably of a maximum of 3 molar equivalents of a Lewis acid as catalyst, hydrolysis is carried out in order to obtain transiently, and without isolation, dronedarone hydrochloride which is recovered in the organic phase and the hydrochloride formed is treated with a basic agent, giving dronedarone.

According to another aspect of the invention, dronedarone may be obtained using a three-stage method starting with 2-butyl-5-nitrobenzofuran.

Consequently, another subject of the invention relates to the preparation of dronedarone starting with 2-butyl-5-nitrobenzofuran according to a method by which:

a) 2-butyl-5-nitrobenzofuran is hydrogenated in the presence of an appropriate catalyst, to form 5-amino-2-butylbenzofuran, b) the compound thus obtained is reacted with methanesulfonyl chloride or methanesulfonic anhydride, the reaction taking place in the presence of an acid acceptor, to form 2-butyl-5-(methanesulfonamido)benzofuran, c) the methanesulfonamido derivative thus obtained is reacted, in an organic phase consisting of one or more solvents chosen from halogenated or nonhalogenated hydrocarbons, with 4-[3-(dibutylamino)propoxy]benzoyl chloride hydrochloride, this being in the presence of a maximum of 5 molar equivalents, in particular of a maximum of 4 molar equivalents and preferably of a maximum of 3 molar equivalents of a Lewis acid as catalyst, hydrolysis is carried out in order to obtain transiently, and without isolation, dronedarone hydrochloride which is recovered in the organic phase and the hydrochloride formed is treated with a basic agent, giving dronedarone.

Subsequently, the dronedarone obtained according to either method or variant of the invention may be treated, if necessary, with an organic or inorganic acid to form a pharmaceutically acceptable salt of this compound.

4-[3-(Dibutylamino)propoxy]benzoyl chloride hydrochloride, for its part, may be prepared according to the succession of steps below:

a) 1-dibutylamino-3-chloropropane is reacted with a $C_1$–$C_4$ alkyl p-hydroxybenzoate, for example methyl p-hydroxybenzoate, this being in the presence of a basic agent such as an alkali metal carbonate, for example potassium carbonate, to give a methyl 4-[3-(dibutylamino)propoxy]benozate, b) the ester thus obtained is saponified in the presence of an alkali metal hydroxide, for example sodium hydroxide, and then the salt thus formed is treated with hydrochloric acid to give 4-[3-(dibutylamino)propoxy]benzoic acid hydrochloride, c) the hydrochloride thus formed is treated with a chlorinating agent, for example thionyl chloride, to give the desired compound.

This use of the method of the invention for the preparation of dronedarone has proved superior to the method of patent EP0471609 in particular because of a smaller number of steps, namely three instead of five starting with 2-butyl-5-nitrobenzofuran and a higher overall yield since it is greater than 65%, or even 70%.

Moreover, this method of the invention involves, in each step, benzofuran intermediates of relatively simple structure, and consequently inexpensive, unlike the earlier method which uses in each of its steps benzofuran derivatives of a fairly elaborate structure.

The following nonlimiting examples illustrate the invention.

PREPARATIONS

A. 1-Dibutylamino-3-chloropropane

Into a 1 l reactor, there are introduced 288.4 g (3.392 mol) of 20% aqueous ammonia, and then there are added, over 10 minutes and at room temperature (22±2° C.), 618 g (1.696 mol) of 1-dibutylamino-3-chloropropane hydrochloride (titer 66.5%). The medium is stirred for 45 minutes at room temperature and it is allowed to separate by settling for 30 minutes. The bottom aqueous phase (pH=11) is removed, and the organic phase is washed with 300 ml of deionized water at room temperature. The medium is stirred for 30 minutes, separated by settling for 30 minutes and the bottom aqueous phase (pH=9) is drawn off.

In this manner, 346.3 g of the desired compound are recovered.

Yield: 99.4%.

B. Methyl 4-[3-(dibutylamino)propoxy]-benzoate 200 g (1.3 mol) of methyl p-hydroxybenzoate and 1.6 l of N,N-dimethylformamide are introduced into a 2 l round-bottomed flask. The mixture is stirred and 232 g (1.66 mol) of potassium carbonate are added thereto. The medium is heated to 100° C. and then the 1-dibutylamino-3-chloropropane prepared in step A. above is introduced over 10 minutes. The reaction medium is kept for 1 hour at 100±2° C. and then cooled to 25° C. The inorganic salts are filtered off and the filtrate is rinsed with twice 50 ml of N,N-dimethylformamide and concentrated in a rotary evaporator until a temperature of 85° C. and a pressure of 5 mmHg are obtained.

In this manner, 472.7 g of the desired product are obtained in the form of an orange oil.

Purity (HPLC or High-performance Liquid Chromatography)

Desired compound: 99.7%

Methyl p-hydroxybenzoate: 0.1%

C. 4-[3-(Dibutylamino)propoxy]benzoic acid hydrochloride 436.3 g of methyl 4-[3-(dibutylamino)-propoxy]benzoate and 1.092 l of methanol are introduced into a 2 l round-bottomed flask. The mixture is stirred and 360 g (1.8 mol) of 20% sodium hydroxide are introduced over about 5 minutes.

The medium is heated at 65° C. for about 30 minutes and kept at this temperature for 2 hours. The reaction medium is cooled to 30° C. and concentrated in a rotary evaporator (temperature of the bath: 30° C., pressure 30 mmHg), which gives 937 g of residue which is diluted by adding 2.8 l of deionized water. The solution is cooled to 10±2° C. and then, without exceeding 20° C., 260 ml (about 3 mol) of a 36% hydrochloric acid are introduced.

It is checked that the pH is less than 1, and then the suspension is cooled to 10±2° C. This temperature is maintained for 30 minutes, the crystals formed are drained and the cake is washed with twice 200 ml of deionized water. It is then dried in a ventilated oven at 50° C. to a constant weight (24 hours).

In this manner, 416.2 g of the desired compound are obtained.

Yield: 100%.

Purity (HPLC)

Desired compound: 99.5%

Methyl 4-[3-(dibutylamino)propoxy]benzoate: 0.1%

D. 4-[3-(Dibutylamino)propoxy]benzoyl chloride hydrochloride 63.3 g (0.184 mol) of 4-[3-(dibutylamino)propoxy] benzoic acid hydrochloride, 300 ml of chlorobenzene and 2 drops of N,N-dimethylformamide are introduced into a round-bottomed flask. 43.8 g (0.368 mol) of thionyl chloride are introduced, over about 45 minutes, while the mixture is kept under an inert atmosphere. The medium is kept for 1 hour at 85±1° C. and then about 115 g of a mixture of chlorobenzene and thionyl chloride is distilled under a gradual vacuum.

In this manner, the desired compound is obtained in the form of an oil and in crude form.

EXAMPLE 1

5-Amino-2-butylbenzofuran

Method I 182 g of 2-butyl-5-nitrobenzofuran and 730 ml of ethanol are introduced into a hydrogenation apparatus, and then 9.1 g of about 97% platinum oxide are added. A hydrogen stream is bubbled through, with stirring at a pressure of 25 bar (the temperature increases spontaneously to 60° C.) and the medium is cooled to 20° C. The medium is filtered, rinsed with 400 ml of ethanol and concentrated at 50° C. under vacuum.

In this manner, 5-amino-2-butylbenzofuran is obtained.

Weight yield: 99.2%

Method II 1 g of 2-butyl-5-nitrobenzofuran and 4 ml of ethanol are introduced into a closed reactor and then 1.48 g of ammonium formate and 0.1 g of 5% palladized charcoal are added. The medium is stirred and heated at 50° C. for 5 hours and then cooled to 20° C., and filtered. The medium is rinsed with 4 ml of ethanol and concentrated at 50° C., under vacuum.

In this manner, 5-amino-2-butylbenzofuran is obtained.

EXAMPLE 2

2-Butyl-5-(methan sulfonamido)benzofuran 100 g of 5-amino-2-butylbenzofuran, 192 ml of tetrahydrofuran and 96 ml of methyl tert-butyl ether are introduced into a round-bottomed flask. 59.35 g of methanesulfonyl chloride are added, at 20° C., followed by 43.23 g of 20% aqueous ammonia. 44.51 g of methanesulfonyl chloride are then introduced, followed by 86.47 g of 20% aqueous ammonia. 48 ml of water are then added, the medium is separated by settling and the organic phase is washed twice with 211 g of 10% aqueous sodium chloride solution. The medium is separated by settling and concentrated at 400° C. under vacuum, to give the desired compound in crude form (weight yield: 100%).

135.6 g of the residue thus obtained are introduced into 1220 ml of methyl tert-butyl ether and 13.56 g of carbon black are added.

The medium is stirred under reflux for 15 minutes, filtered and rinsed with 204 ml of methyl tert-butyl ether. The filtrate is heated under reflux and then cooled to 400° C. The medium is then seeded with 2-butyl-3-(methanesulfonamido)benzofuran, cooled to −5° C. and stirred at this temperature for 30 minutes.

The medium is filtered and rinsed at −50° C. with twice 1 volume of methyl tert-butyl ether.

In this manner, the desired compound is obtained with a weight yield of 78.5%.

NMR (Nuclear Magnetic Resonance) Spectrum (300 MHz)
Solvent: $CDCl_3$
Concentration: 40 mg/ml
Temperature for analysis: 300 K

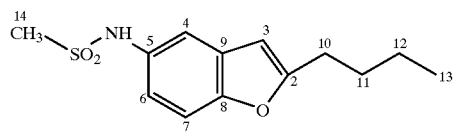

| Chemical shifts δ ± 0.01 ppm | Multiplicity | Integration | Coupling constant $|J| \pm 0.5$ Hz | Attribution |
|---|---|---|---|---|
| 7.42 | doublet | 1 | $^4J_{H-H} \approx 2.0$ | H(4) |
| 7.36 | doublet | 1 | $^3J_{H-H} \approx 8.5$ | H(7) |
| 7.08 | doublet of doublets | 1 | $^3J_{H-H} \approx 8.5$ $^4J_{H-H} \approx 2.0$ | H(6) |
| 6.83–6.89 | broad signals | 1 | — | NH |
| 6.35 | singlet | 1 | — | H(3) |
| 2.97 | singlet | 3 | — | $CH_3SO_2$ |
| 2.76 | triplet | 2 | $^3J_{H-H} \approx 7.5$ | $CH_2(10)$ |
| 1.72 | quintuplet | 2 | $^3J_{H-H} \approx 7.5$ | $CH_2(11)$ |
| 1.42 | sextuplet | 2 | $^3J_{H-H} \approx 7.5$ | $CH_2(12)$ |
| 0.95 | triplet | 3 | $^3J_{H-H} \approx 7.5$ | $CH_3(13)$ |

EXAMPLE 3

Dronedarone Hydrochloride

A mixture of 8 g of 2-butyl-5-(methanesulfonamido)benzofuran, 11.9 g of 4-[3-(dibutylamino)propoxy]benzoyl chloride hydrochloride and 24 ml of dichloromethane is first of all prepared. This mixture is then introduced into a medium consisting of 11.9 g of ferric chloride and 24 ml of dichloromethane. The reaction medium is heated under reflux for 2 hours and cooled to 20° C. 40 ml of water are added and the medium is separated by settling.

In this manner, dronedarone hydrochloride is obtained in crude form.

Chemical yield: 90%.

EXAMPLE 4

Dronedarone Hydrochloride

A. Dronedarone

The dronedarone hydrochloride obtained in Example 3 above is washed twice, this being with 24 ml of water, and then with 16 ml of a 10% aqueous sodium hydroxide solution and finally with 16 ml of water.

In this manner, dronedarone in crude form is obtained.
Chemical yield: 86%.

B. Dronedarone Hydrochloride

The dronedarone in crude form obtained in the preceding paragraph A. is concentrated and taken up in 24 ml of isopropanol. 3.24 g of 37% hydrochloric acid are added and then the medium is cooled to 0° C. The medium is filtered and washed with 8 ml of isopropanol.

In this manner, dronedarone hydrochloride is obtained.

EXAMPLE 5

Dronedarone Hydrochloride—Preparation on a Pilot Scale 5.1. Dronedarone hydrochloride A mixture of 10 kg of 2-butyl-5-(methanesulfonamido)benzofuran, 13 kg of 4-[3-(dibutylamino)propoxy]benzoyl hydrochloride and 70 l of dichloromethane is first of all prepared. 19.9 kg of aluminum chloride are then introduced into this mixture (4 molar equivalents of Lewis acid are thus used; 2.5 molar equivalents of ferric chloride were used for the above Example 3). The medium is stirred at 25° C. for two hours. This medium is added to 60 l of water and the medium is separated by settling.

In this manner, dronedarone hydrochloride in crude form is obtained.

Chemical yield=90%.

5.2. Dronedarone and then Dronedarone Hydrochloride

The dronedarone hydrochloride obtained in the preceding step is washed 5 times with 60 l of water. The dronedarone is concentrated and taken up in 94 l of isopropanol. 1.8 kg of water and 0.38 kg of hydrochloric acid are added. The medium is cooled to −5° C. The medium is filtered, and washed with 22 l of isopropanol.

In this manner, dronedarone hydrochloride is obtained.
Chemical yield=90%.

What is claimed is:

1. 2-Butyl-5-(methanesulfonamido)benzofuran.

2. A method for preparing 2-butyl-5-(methanesulfonamido)benzofuran, wherein 5-amino-2-butylbenzofuran is reacted with methanesulfonyl chloride or methanesulfonic anhydride, the reaction taking place in the presence of an acid acceptor, giving the desired compound.

3. A method for preparing dronedarone, wherein, in an organic phase consisting of one or more solvents chosen from halogenated or nonhalogenated hydrocarbons, 2-butyl-5-(methanesulfonamido)benzofuran is reacted with 4-[3-(dibutylamino)propoxy]benzoyl chloride hydrochloride, this being in the presence of a maximum of 5 molar equivalents of a Lewis acid as catalyst, and then hydrolysis is carried out so as to form dronedarone hydrochloride which is recovered in the organic phase, which is isolated and which is treated with a basic agent, to give the desired compound.

4. The method as claimed in 3, wherein 2-butyl-5-(methanesulfonamido)benzofuran is reacted with 4-[3-(dibutylamino)propoxy]benzoyl chloride hydrochloride in the presence of a maximum of 4 molar equivalents of the Lewis acid.

5. The method as claimed in 4, wherein 2-butyl-5-(methanesulfonamido)benzofuran is reacted with 4-[3-(dibutylamino)propoxy]benzoyl chloride hydrochloride in the presence of a maximum of 3 molar equivalents of the Lewis acid.

6. A method for preparing dronedarone, wherein, in an organic phase consisting of one or more solvents chosen from halogenated or nonhalogenated hydrocarbons, 2-butyl-5-(methanesulfonamido)benzofuran is reacted with 4-[3-(dibutylamino)propoxy]benzoyl chloride hydrochloride, this being in the presence of a maximum of 5 molar equivalents of a Lewis acid as catalyst, and then hydrolysis is carried out in order to obtain transiently, and without isolation, dronedarone hydrochloride which is recovered in the organic phase and which is treated with a basic agent, giving the desired compound.

7. The method as claimed in claim 6, wherein 2-butyl-5-(methanesulfonamido)benzofuran is reacted with 4-[3-(dibutylamino)propoxy]benzoyl chloride hydrochloride in the presence of a maximum of 4 molar equivalents of the Lewis acid.

8. The method as claimed in 7, wherein 2-butyl-5-(methanesulfonamido)benzofuran is reacted with 4-[3-(dibutylamino)propoxy]benzoyl chloride hydrochloride in the presence of a maximum of 3 molar equivalents of the Lewis acid.

9. A method for preparing dronedarone, wherein:
a) 2-butyl-5-nitrobenzofuran is hydrogenated in the presence of an appropriate catalyst, to form 5-amino-2-butylbenzofuran,
b) the compound thus obtained is reacted with methanesulfonyl chloride or in ethanesulfonic anhydride, the reaction taking place in the presence of an acid acceptor, to form 2-butyl-5-(methanesulfonamido)benzofuran,
c) the methanesulfonamido derivative thus obtained is reacted, in an organic phase consisting of one or more solvents chosen from halogenated or nonhalogenated hydrocarbons, with 4-[3-(dibutylamino)propoxy]benzoyl chloride hydrochloride, this being in the presence of a maximum of 5 molar equivalents of a Lewis acid as catalyst, and then hydrolysis is carried out in order to obtain transiently, and without isolation, dronedarone hydrochloride which is recovered in the organic phase and which is treated with a basic agent, giving the desired compound.

10. The method as claimed in claim 9, wherein in step c), the methanesulfonamido derivative thus obtained is reacted with 4-[3-(dibutylamino)propoxy]benzoyl chloride hydrochloride in the presence of a maximum of 4 molar equivalents of the Lewis acid.

11. The method as claimed in 10, wherein in step c), the methanesulfonamido derivative thus obtained is reacted with 4-[3-(dibutylamino)-propoxy]benzoyl chloride hydrochloride in the presence of a maximum of 3 molar equivalents of the Lewis acid.

12. The method as claimed in claim 3 wherein the organic phase consists of one or more solvents chosen from halogenated hydrocarbons of the aliphatic, alicyclic or aromatic type.

13. The method as claimed in claim 3 wherein the Lewis acid is chosen from the group consisting of aluminum chloride, zinc chloride, boron trifluoride, stannic chloride, titanium tetrachloride, ferric chloride and mixtures thereof.

14. The method as claimed in claim 3 wherein the Lewis acid is ferric chloride.

15. The method as claimed in claim 3 wherein the Lewis acid is used in an amount of 2 to 5 molar equivalents.

16. The method as claimed in claim 3 wherein the Lewis acid is used in an amount of 2 to 3 molar equivalents.

17. The method as claimed in claim 3 wherein the 4-[3-(dibutylamino)propoxy]benzoyl chloride hydrochloride is used at concentrations of the order of 1 to 1.3 molar equivalents.

18. The method as claimed in claim 3 wherein the basic agent is sodium hydroxide or sodium hydrogen carbonate.

19. The method as claimed in claim 6 wherein the organic phase consists of one or more solvents chosen from halogenated hydrocarbons of the aliphatic, alicyclic or aromatic type.

20. The method as claimed in claim 9 wherein the organic phase consists of one or more solvents chosen from halogenated hydrocarbons of the aliphatic, alicyclic or aromatic type.

21. The method as claimed in claim 6 wherein the Lewis acid is chosen from the group consisting of aluminum chloride, zinc chloride, boron trifluoride, stannic chloride, titanium tetrachloride, ferric chloride and mixtures thereof.

22. The method as claimed in claim 9 wherein the Lewis acid is chosen from the group consisting of aluminum chloride, zinc chloride, boron trifluoride, stannic chloride, titanium tetrachloride, ferric chloride and mixtures thereof.

23. The method as claimed in claim 12 wherein the Lewis acid is chosen from the group consisting of aluminum chloride, zinc chloride, boron trifluoride, stannic chloride, titanium tetrachloride, ferric chloride and mixtures thereof.

24. The method as claimed in claim 6 wherein the Lewis acid is ferric chloride.

25. The method as claimed in claim 9 wherein the Lewis acid is ferric chloride.

26. The method as claimed in claim 12 wherein the Lewis acid is ferric chloride.

27. The method as claimed in claim 13 wherein the Lewis acid is ferric chloride.

28. The method as claimed in claim 6 wherein the Lewis acid is used in an amount of 2 to 5 molar equivalents.

29. The method as claimed in claim 9 wherein the Lewis acid is used in an amount of 2 to 5 molar equivalents.

30. The method as claimed in claim 13 wherein the Lewis acid is used in an amount of 2 to 5 molar equivalents.

31. The method as claimed in claim 14 wherein the Lewis acid is used in an amount of 2 to 5 molar equivalents.

32. The method as claimed in claim 6 wherein the Lewis acid is used in an amount of 2 to 3 molar equivalents.

33. The method as claimed in claim 9 wherein the Lewis acid is used in an amount of 2 to 3 molar equivalents.

34. The method as claimed in claim 13 wherein the Lewis acid is used in an amount of 2 to 3 molar equivalents.

35. The method as claimed in claim 14 wherein the Lewis acid is used in an amount of 2 to 3 molar equivalents.

36. The method as claimed in claim 6 wherein the 4-[3-(dibutylamino)propoxy]benzoyl chloride hydrochloride is used at concentrations of the order of 1 to 1.3 molar equivalents.

37. The method as claimed in claim 9 wherein the 4-[3-(dibutylamino)propoxy]benzoyl chloride hydrochloride is used at concentrations of the order of 1 to 1.3 molar equivalents.

38. The method as claimed in claim 12 wherein the 4-[3-(dibutylamino)propoxy]benzoyl chloride hydrochloride is used at concentrations of the order of 1 to 1.3 molar equivalents.

39. The method as claimed in claim 13 wherein the 4-[3-(dibutylamino)propoxy]benzoyl chloride hydrochloride is used at concentrations of the order of 1 to 1.3 molar equivalents.

40. The method as claimed in claim 14 wherein the 4-[3-(dibutylamino)propoxy]benzoyl chloride hydrochloride is used at concentrations of the order of 1 to 1.3 molar equivalents.

41. The method as claimed in claim 15 wherein the 4-[3-(dibutylamino)propoxy]benzoyl chloride hydrochloride is used at concentrations of the order of 1 to 1.3 molar equivalents.

42. The method as claimed in claim 16 wherein the 4-[3-(dibutylamino)propoxy]benzoyl chloride hydrochloride is used at concentrations of the order of 1 to 1.3 molar equivalents.

43. The method as claimed in claim 6 wherein the basic agent is sodium hydroxide or sodium hydrogen carbonate.

44. The method as claimed in claim 9 wherein the basic agent is sodium hydroxide or sodium hydrogen carbonate.

45. The method as claimed in claim 12 wherein the basic agent is sodium hydroxide or sodium hydrogen carbonate.

46. The method as claimed in claim 13 wherein the basic agent is sodium hydroxide or sodium hydrogen carbonate.

47. The method as claimed in claim 14 wherein the basic agent is sodium hydroxide or sodium hydrogen carbonate.

48. The method as claimed in claim 15 wherein the basic agent is sodium hydroxide or sodium hydrogen carbonate.

49. The method as claimed in claim 16 wherein the basic agent is sodium hydroxide or sodium hydrogen carbonate.

50. The method as claimed in claim 17 wherein the basic agent is sodium hydroxide or sodium hydrogen carbonate.

* * * * *